(12) United States Patent
Rausch et al.

(10) Patent No.: US 6,448,424 B1
(45) Date of Patent: Sep. 10, 2002

(54) TETRAHYDROFLUORENYL CONTAINING GROUP 4 METALLOCENES USEFUL AS CATALYSTS FOR THE POLYMERIZATION OF OLEFINS, PROCESS FOR THEIR PREPARATION AND USE OF SAID METALLOCENES FOR THE POLYMERIZATION OF OLEFINS

(75) Inventors: Marvin D. Rausch; Emma J. Thomas, both of Amherst, MA (US); Serge Bettonville, Crisnee (BE)

(73) Assignee: Solvay Polyolefins Europe-Belgium (Société Anonyme), Brussels (BE)

( * ) Notice: Subject to any disclaimer, the term of this patent is extended or adjusted under 35 U.S.C. 154(b) by 0 days.

(21) Appl. No.: 09/562,861

(22) Filed: May 1, 2000

(51) Int. Cl.⁷ .................................................. C07F 7/08
(52) U.S. Cl. ............................ 556/11; 556/53; 556/51; 502/152; 526/127; 526/160; 526/170; 526/943
(58) Field of Search .................................. 526/160, 170, 526/943; 556/51–53, 11

(56) References Cited

U.S. PATENT DOCUMENTS 5,453,410 A * 9/1995 Kolthammer et al. ....... 502/155
5,670,680 A * 9/1997 Newman et al. ............... 556/53
5,814,714 A * 9/1998 Palomo et al. ............... 526/336
5,945,365 A * 8/1999 Reddy ........................ 502/117
6,100,416 A   8/2000 Rausch

OTHER PUBLICATIONS

J. Colonge et al., Bull. Chim. Soc. Fr., 1952, pp. 786–789.
J. Colonge et al., Bull. Chim, Soc. Fr., 1953, pp. 75–78.
U.S. patent application Ser. No. 09/376,179.
Resconi et al. Organometallics 1996, 15, 998–1005.*
Cologne, J. and Sibeud, J. Bull. Chim. Soc. Fr. 1953, 75–78.*
Cologne, J. and Sibeud, J. Bull. Chim. Soc. Fr. 1952, 786–789.*

* cited by examiner

Primary Examiner—David W. Wu
Assistant Examiner—Rip A. Lee
(74) Attorney, Agent, or Firm—Venable; Marina V. Schneller

(57) ABSTRACT

Novel silylene or ethylene bis(tetrahydrofluorenyl) metallocenes are synthesized and used as olefin polymerization catalysts.

1 Claim, No Drawings

TETRAHYDROFLUORENYL CONTAINING GROUP 4 METALLOCENES USEFUL AS CATALYSTS FOR THE POLYMERIZATION OF OLEFINS, PROCESS FOR THEIR PREPARATION AND USE OF SAID METALLOCENES FOR THE POLYMERIZATION OF OLEFINS

TECHNICAL FIELD

The present invention relates to novel tetrahydrofluorenyl containing Group 4 metallocenes as catalysts for the polymerization of olefins. It relates more specifically to novel silylene or ethylene bis(tetrahydrofluorenyl) metallocenes and to their use for polymerizing olefins. Finally, it relates to a process for preparing said metallocenes.

BACKGROUND OF THE INVENTION

The use of bis(fluorenyl) metallocenes for polymerizing olefins has already been described. However most of these metallocenes are unstable due to internal ligand rearrangements and cannot be used in an economic way.

SUMMARY OF THE INVENTION

It is an object of the present invention to solve the above problem by providing novel bis(tetrahydrofluorenyl) metallocenes useful as catalysts for olefin polymerization, which are stable. More particularly it is an object of the invention to provide bis(tetrahydrofluorenyl) metallocenes which are able to produce, with a particularly high activity, polyethylene having high molecular weight or polyethylene having a broad or even a bimodal molecular weight distribution. It is another object of the present invention to provide a process for polymerization of olefins by means of said metallocenes and a process for preparing said novel metallocenes.

The invention is thus related to novel metallocenes represented by the general formula

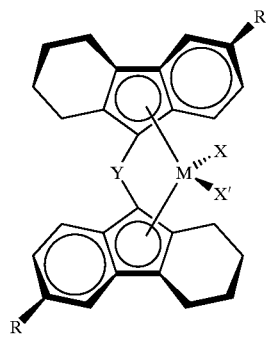

wherein:
M represents a group 4 transition metal,
X and X' represent a halogen atom,
R represents an alkyl or aryl group containing from 1 to 10 carbon atoms or a hydrogen atom, and
Y represents an ethylene group or a silylene group of formula $SiR^1R^2$ where $R^1$ and $R^2$ represent each independently an alkyl or aryl radical containing from 1 to 10 carbon atoms,
said metallocene being usable for the polymerization of olefins.

The invention also relates to a process for the preparation of metallocenes according to the invention comprising the following steps:
a) preparation of 2-benzylcyclohexanone or substituted derivatives thereof by reaction of 2-sodio-cyclohexanone with benzyl chloride or substituted derivatives thereof,
b) production of the tetrahydrofluorenyle compounds by reaction of the 2-benzylcyclohexanones with aluminum trichloride,
c) production of the ethylene or dialkylsilylene bridged ligands by reacting the tetrahydrofluorenyle compounds successively with butyllithium and 1,2-dibromoethane or dichlorodialkyl- or arylsilane, and
d) production of the bridged bis(tetrahydrofluorenyl) metallocene by reacting the said ligands successively with butyllithium and metal tetrahalide.

DETAILED DESCRIPTION

According to a first aspect, the present invention relates to novel metallocenes of the above general formula.

Preferably the transition metal M is selected from hafnium and zirconium. Most preferably the transition metal is zirconium.

The halogen atoms X and X' are preferably chlorine or bromine atoms and most preferably they are both chlorine atoms.

The radical R represents preferably an alkyl group containing from 1 to 3 carbon atoms or a hydrogen atom.

The silylene group is advantageously such that the radicals $R^1$ and $R^2$ are alkyl radicals and more particularly alkyl radicals containing from 1 to 3 carbon atoms.

The novel metallocenes according to the present invention are very stable. They are useful as catalysts for the polymerization of olefins. The reaction is carried out by contacting said olefins with the said metallocene under polymerization conditions. It can be carried out in solution or in suspension in a hydrocarbon diluant or in suspension in the, or one of the, monomer(s) maintained in the liquid form or in the gas phase. The polymerization conditions are well known by the man of ordinary skill in the art.

The metallocenes according to the invention can be used in combination with one another. They can also be used in combination with aluminoxanes. Methylaluminoxane is preferred. They can also be used in combination with an ionizing agent. This ionizing agent can be chosen from the compounds comprising a first part which has the properties of a Lewis acid and which is capable of ionizing the metallocene and a second part that is inert towards the ionized metallocene. Examples of ionizing agents are triphenylcarbenium tetrakis(pentafluorophenyl) borate, N,N'-dimethyl anilinium tetrakis(pentafluorophen l) borate, tri(n-butyl)ammonium tetrakis(pentafluorophenyl)borate, tri(pentafluorophenyl)boron, triphenylboron, trimethylboron, tri(trimethylsilyl)borate and organoboroxines.

During the polymerization, organometallic compounds may be added to the polymerization medium as cocatalysts and/or poison scavengers. They can be selected from organometallic compounds of lithium, magnesium, zinc, aluminum or tin. The best results are obtained with organoaluminium compounds and in particular with trialkylaluminium compounds.

The olefins to be polymerized can be chosen from those containing up to 20, preferably up to 8 carbon atoms per molecule. The olefin is preferably ethylene. The metallocenes according to the present invention may be used for the homopolymerization of one of these olefins or for the copolymerization—random or block copolymerization—of one of these olefins with one or more comonomers. The preferred comonomers of ethylene are propylene, butene, hexene and their mixtures.

It has been noted that metallocenes according to the invention wherein both R are alkyl makes it possible to obtain polyethylene polymers with very high activity. It is also noted that metallocenes according to the invention in which Y is dialkyl or diaryl silylene are able to produce polyethylenes of high molecular weight. The use of metallocenes wherein both R are hydrogen atoms makes it possible to obtain of polyethylenes having a broad or a bimodal distribution of the molecular weight. Such polymers are particularly easily molded according to any known process.

Metallocenes of formula

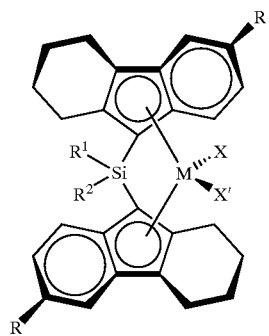

wherein R is chosen from alkyl having from 1 to 3 carbon atoms, M is zirconium, X and X' are chlorine atoms and $R^1$ and $R^2$ are each alkyl radical containing 1 to 3 carbon atoms are particularly advantageous for the production, with high activity, of polyethylene having high molecular weight.

According to a second aspect, the present invention relates to a process for producing the novel metallocenes according to the present invention.

The said process comprises the following steps
a) preparation of 2-benzylcyclohexanone or the substituted derivatives thereof by reaction of 2-sodio-cyclohexanone with benzyl chloride or substituted derivatives thereof,
b) production of the tetrahydrofluorenyle compounds by reaction of the 2-benzylcyclohexanones with aluminum trichloride,
c) production of the ethylene or dialkylsilylene bridged ligands by reacting the tetrahydrofluorenyle compounds successively with butyllithium and 1,2-dibromoethane or dichlorodialkyl or arylsilane, and
d) production of the bridged bis(tetrahydrofluorenyl) metallocenes by reacting the said ligands successively with butyllithium and metal tetrahalide.

The general conditions of steps (a) and (b) are disclosed in Bull. Chem. Soc. Fr. 1952, 786 and 1953, 75 which are incorporated herein by reference.

In step (a), 2-sodio-cyclohexanone and the benzyl chlorides are reacted in about equivalent molar quantities.

Preferably, step (b) is carried out by adding about 3 moles of aluminium trichloride per mole of benzylcyclohexanone.

Step (c) is preferably carried out by adding about one equivalent of butyllithium and a half equivalent of 1,2 dibromoethane or dichlorodialkyl or arylsilane per equivalent of tetrahydrofluorenyle compound.

Step (d) is most often carried out by reacting first about two equivalents of butyllithium per equivalent of the bis (tetrahydrofluorenyl) ligand to obtain a solid that is then treated with one equivalent metal tetrahalide per equivalent of the tetrahydrofluorenyle ligand.

Preferably, reaction step (a) is carried out in an inert solvent, for example an ether and more particularly anhydrous diethyl ether. Reaction step (a) is usually carried out at a temperature in the range of 25–85° C. At the end of reaction of step (a), the solvent is generally removed in order to separate the produced benzylcyclohexanone.

Preferably, the step (b) is carried out in an inert solvent such as hexane or other alkane, most often at about 50–90° C. At the end of the reaction, the tetrahydrofluorenyle compound is usually isolated in the form of white crystals by crystallization from methanol.

Preferably, step (c) is carried out in an inert solvent, such as an ether, most often in tetrahydrofuran. The temperature is usually in the range of about minus 10° C. to about room temperature. Temperature of about 0° C. is the most advantageous. The reaction is usually carried out by adding first the butyllithium to the tetrahydrofluorenyle compound. The reaction medium was then usually stirred for a period of from 2 to 10 hours before adding the 1,2 dibromoethane or the dichlorodialkyl or arylsilane. The resulting bis (tetrahydrofluorenyl) ligand is then advantageously separated from its preparation medium and recrystallized.

Step (d) is preferably carried out in an inert solvent, such as diethyl ether at a temperature of between minus 10° C. to 10° C., preferably at about 0° C. by addition of about two equivalents of butyllithium per equivalent of the bis (tetrahydrofluorenyl) ligand. The obtained solid was then usually reacted, after isolation, with about one equivalent of the metal tetrahalide. After removal of the solvent, the solid metallocene is isolated preferably by extraction into dichloromethane, concentration and cooling to −20° C.

In addition to the foregoing description of the invention, the following examples, are provided t illustrate the present invention.

In these examples, reactions are carried out under an argon atmosphere using standard Schlenk techniques. Diethyl ether, tetrahydrofuran (THF) and pentane were distilled from Na/K alloy under argon. Dichloromethane was distilled from $CaH_2$ under argon.

Melting points of the polymers were determined by DSC with a Perkin-Elmer DSC-System. $^{13}C$ NMR spectra were determined on a DPX300/AMX500 spectrometer in $CDCl_3$ at room temperature, and at 80° C. in $C_6D_5Cl$. $^1H$ NMR spectra were recorded only an AC-200 spectrometer.

A. Preparation of metallocenes

EXAMPLE 1

Preparation of the ethylene bis(tetrahydrofluorenyl) zirconium dichloride

Preparation of 2-benzylcyclohexanone [step (a)]

Sodium amide (15.6 g, 0.4 mol) was added portionwise to a solution of cyclohexanone (39.26 g, 1.46 mL, 0.4 mol) in 350 mL of anhydrous diethyl ether. The resulting suspension was heated under reflux for 3 h after which time benzyl chloride (46.8 g, 42.6 mL, 0.37 mol) was rapidly added. The mixture was heated under reflux for a further 5 h, then cooled and poured into cold water. The organics were washed once with a dilute HCl solution, a dilute sodium bicarbonate solution and finally with water. The organic layer was dried, filtered and the ether was removed to give 2-benzylcyclohexanone as an oil (28 g, 40%).

Preparation of tetrahydrofluorene [step (b)]

Aluminium chloride (53.7 g, 0.40 mol) was added portionwise to 2-benzylcyclohexanone (25 g, 0.13 mol) in 100 mL of hexane. The mixture was heated at 60° C. for 4 h then cooled and poured onto ice acidified with HCl (aq). The organic layer was decanted and the aqueous layer was extracted with 100 mL of hexane. The organics were washed once with a dilute HCl solution, a dilute sodium bicarbonate solution and finally with water. The organic layer was dried, filtered and the hexane was removed. The resulting oil was distilled at 110–135° C. at 4 mm Hg, followed by crystallization from methanol gave (5 g, 23%) of tetrahydrofluorene as a white solid, mp 57° C.

Preparation of bis(tetrahydrofluorenyl)ethane [step (c)]

Tetrahydrofluorene (17.6 mmol) was dissolved in 20 ml of dry THF and cooled to 0° C. Butyllithium, (11 ml of a solution 1.6M in hexane, 17.6 mmol) was added dropwise to give a red/orange solution that was stirred for 6h. 1,2-dibromoethane (1.66 g, 8.81 mmol) was added quickly. The resulting beige suspension was stirred overnight. The mixture was hydrolyzed with $NH_4Cl$ and extracted in THF and diethyl ether. The organics were collected, dried, filtered and the solvents were removed to give a yellow solid.

Recrystallization from toluene/hexane 1:1 resulted in 1.949 g (60%) of bis(tetrahydrofluorenyl)ethane as a white solid; mp 186–187° C., $^1$H NMR (CDCl$_3$): δ7.28–7.07 (m, 8H, arom), 3.14 (bs, 2H, C$_5$), 2.41–2.13 (m, 8H), 1.80–1.77 (m, 4H), 1.51–1.27 (m 4H). Analysis calculated for $C_{28}H_{30}$: C, 91,75; H, 8.25. Found C, 91.47; H, 8.34.

Preparation of ethylene bis(tetrahydrofluorenyl) zirconium dichloride [step(d)]

To a suspension of bis(tetrahydrofluorenyl)ethane (1.00 g, 2.73 mmole) in 30 ml of dry diethyl ether at 0° C. was added 2 equivalents butyllithium (1.6 molar in hexane, 3.41 ml, 5.46 mmol). The resulting yellow suspension was stirred for 6 h. The solvent was removed in vacuum and the solid was washed with pentane. The solid was suspended in 30 ml of diethyl ether at 0° C. and ZrCl$_4$ (0.64 g, 2.73 mmol) was added as a solid. The mixture was stirred overnight and the solvent was removed by filtration. The yellow solid was extracted in CH$_2$Cl$_2$, concentrated and stored at −20° C. to give ethylene bis(tetrahydrofluorenyl)-zirconium dichloride (0.66 g, 46%), a yellow solid as a mixture of two isomers. $^1$H NMR (CDCl$_3$): δ7.69–6.83 (m, 8H, arom), 5.30 (s, 0.8H, CH$_2$Cl$_2$), 4.09–3.69 (m, 4H, bridge), 3.21–2.41 (m, 8H), 2.20–1.30 (m, 8H). Analysis calculated for $C_{28}H_{28}Cl_2Zr$ 0.4CH$_2$Cl$_2$: C, 60.84; H, 5.18. Found C, 61.05; H, 5.23.

EXAMPLE 2

Preparation of dimethylsilylene bis (tetrahydrofluorenyl)zirconium dichloride

Tetrahydrofluorene is prepared as described in example 1.

Preparation of bis(tetrahydrofluorenyl) dimethylsilane

Following the procedure described in example 1 [step (c)], tetrahydrofluorene (17.6 mmol), butyllithium (11 ml of a solution 1.6M in hexane, 17.6 mmol) and dichlorodimethylsilane (1.07 ml, 8.81 mmol) gave a yellow oil.

Recrystallization from hexane resulted in 1.33 g (38%) of bis(tetrahydrofluorenyl)dimethylsilane as a white solid (mixture of two isomers); mp 101–102° C. $^1$H NMR (CDCl$_3$): δ7.49–7.06 (m, 8H, arom), 3.59–3.52 (bd, 2H, C$_5$), 2.51–2.38 (m, 8H), 1.93–1.51 (m, 8H), −0.22–0.40 (m, 6H SiCH$_3$). Analysis calculated for $C_{28}H_{32}Si$: C, 84.79; H, 8.13. Found C, 84.98; H, 8.13.

Preparation of dimethylsilylene bis (tetrahydrofluorenyl)zirconium dichloride

Following the procedure described in example 1 [step(d)], bis(tetrahydrofluorenyl)dimethylsilane (1.00 g, 2.52 mmol), 3.15 ml of a butyllithium solution at 1.6 mol (3.15 mL 5.04 mmol) and ZrCl$_4$ (0.59 g, 2.52 mmol) gave dimethylsilylene bis(tetrahydrofluorenyl)zirconium dichloride (0.65 g, 46%), an orange solid as a mixture of two isomers. $^1$H NMR (CDCl$_3$): δ7.66–6.70 (m, 8H, arom), 3.16–2.42 (m, 8H), 2.15–1.45 (m, 8H), 1.42 (s, 1.5H, Si—CH$_3$), 1.25 (s, 3H, Si—CH$_3$), 1.12 (s, 1.5H, SiCH$_3$). Analysis calculated for $C_{28}H_{30}Cl_2SiZr$: C, 60.40; H, 5.43. Found C, 60.22; H, 5.56.

EXAMPLE 3

Preparation of the ethylene bis(3-methyltetrahydrofluorenyl)-zirconium dichloride Preparation of 2-[(4-methyl-benzyl]cyclohexanone Following the procedure described in example 1 [step (a))], sodium amide (14.8 g, 0.38 mol), cyclohexanone (37.30 g, 39.38 mL, 0.38 mol) and 2-methyl benzyl chloride (49.21 g, 46.34 mL 0.35 mol) gave 2-[(4-methyl)benzyl] cyclohexanone as an oil (46.5 g, 66%).

Preparation of 3-methyltetrahydrofluorene

Following the procedure described in example 1 [step (b)], 2-[(4-methyl)benzyl] cyclohexlanone (25 g, 0.12 mol) and aluminum chloride (49.3 g, 0.37 mol) gave 3-methyltetrahydrofluorene as an oil which was purified by distillation at 125–130° C. at 4 mm Hg, followed by crystallization from methanol to give (4.4 g, 19.5%) of3-methyltetrahydrofluorene as a white solid, mp 45.5° C.

Preparation of bis(3-methyltetrahydrofluorenyl) ethane

Following the procedure described in example 1 [step (c)], 3-methyltetrahydrofluorene[(3].00 g, 16.3 mmol), butyllithium (10.20 mL, 16.30 mmol) and 1,2-dibromoethane (1.53 g, 8.15 mmol) were reacted. After addition of the dibromoethane, the reaction mixture was heated to reflux overnight, resulting in a light brown solid after work up which was recrystallized from 100% ethanol to give bis(3-methyltetrahydrofluorenyl)ethane (0.82g, 25%) as a white solid; mp 162–168° C. $^1$H NMR (CDCl$_3$): δ7.17–6.91 (m, 6H, arom), 3.10 (bs, 2H, C$_5$), 2.39 (bs, 10H, CH$_3$ and bridge), 2.23–2.13 (m, 4H), 1.79–1.76 (m, 8H), 1.45–1.43 (m, 4H). Analysis calculated for $C_{30}H_{34}$: C, 91.32; H, 8.68. Found C, 91.32; H, 8.58.

Preparation of ethylene bis(3-methyltetrahydrofluorenyl) zirconium dichloride

Following the procedure described in example 1 [step (d)], bis(3-methyltetrahydrofluorenyll)ethane (0.60 g, 1.52 mmol), butyllithium (1.90 mL 3.04 mmol) and ZrCl$_4$ (0.35 g, 1.52 mmol) gave ethylene bis(3-methyltetrahydrofluorenyl)-zirconium dichloride (0.34 g, 40%), a yellow solid as a mixture of two isomers. $^1$H NMR (CDCl$_3$): δ7.59–6.91 (m, 6H, arom), 3.91–3.63 (m, 4H, bridge), 3.00–2.53 (m, 8H), 2.47–2.46 (d, 6H, CH$_3$) 1.83—1.45(m, 8H). Analysis calculated for $C_{30}H_{32}Cl_2Zr$: C, 64.96; H, 5.81. Found C, 63.27; H, 5.80.

EXAMPLE 4

Preparation of dimethylsilylene bis-(3-methyltetrahydrofluorenyl)-zirconium dichloride 3-methyltetrahydrofluorene is prepared as described in example 3.

Preparation of bis-(3-methyltetrahydrofluorenyl) dimethylsilane

Following the procedure described in example 1 [step (c)], 3methyltetrahydrofluorene (3.00 g, 16.3 mmol), butyl-lithium (16.30 mmol) and dichlorodimethylsilane (0.99 ml, 8.15 mmol) gave bis-(3-methyltetrahydro-fluorenyl) dimethylsilane (1.00 g, 29%) as a white solid that was recrystallized from hexane; mp 179–180° C., $^1$H NMR (CDCl$_3$): δ7.38–6.90 (m, 6H, arom), 3.47 (s, 2H, C$_5$), 2.50–2.45 (m, 8H), 2.48 (s, 6H, CH$_3$), 1.87–1.58 (m, 8H), −0.27 (s, 6H, Si—CH$_3$). Analysis calculated for C$_{30}$H$_{36}$Si: C, 84.84; H, 8.54. Found C, 84.57; H, 8.70.

Preparation of dimethylsilylene bis(3-methyltetrahydrofluorenyl)-zirconium dichloride Following the procedure described in example 1 [step (d)], bis-(3-methyltetrahydrofluorenyl)dimethylsilane (0.65 g, 1.53 mmol), butyllithium (3.06 mmol) and ZrCl$_4$ (0.36 g, 1.53 mmol) gave dimethylsilylene bis(3-methyltetrahydrofluorenyl)zirconium dichloride (0.35 g, 39%), an orange solid as a mixture of two isomers. $^1$H NMR (CDCl$_3$): δ7.51–6.56 (m, 6H, arom), 3.10–2.50 (m, 8H), 2.45 (minor), 2.36 (major), 2.32 (minor) (s, 6H, CH$_3$), 2.09–1.44 (m, 8H), 1.37 (s, 1.5H, Si—CH$_3$), 1.22 (s, 3H, Si—CH$_3$), 1.08 (s, 1.5H, Si—CH$_3$). Analysis calculated for C$_{30}$H$_{34}$Cl$_2$SiZr: C, 61.61; H, 5.86. Found C, 60.63; H, 5.83.

B. Polymerization of olefins General conditions

A 250 ml crown capped glass pressure reactor containing 50 ml of toluene was equilibrated with the appropriate monomer and pressure at the desired temperature. The desired amount of methylaluminoxane (MAO) was added and the solution was stirred for 5 min. 1 ml of the appropriate metallocene catalyst solution in toluene was added and the mixture was stirred until the desired reaction time was reached. The mixture was quenched with 2% HCl in methanol, filtered and dried in a vacuum oven at an appropriate temperature for the polymer sample.

EXAMPLES 5 to 8

These examples are related to the polymerization of ethylene under the general conditions described hereabove by using the catalyst described in examples 1 to 4. The polymerization conditions are as follows: Zr=5 μM; monomer pressure=15 psi, methylaluminoxane is used in a ratio Al/Zr of 4000:1, polymerization temperature=50° C., duration=10 min The activity of the catalyst is expressed in g polymer/(mol Zr* [ethylene]*hour), the melting point Tm is determined by DSC.

The results of these tests are given in Table 1 hereunder.

TABLE 1

| example | catalyst | Yield | activity | Tm |
| --- | --- | --- | --- | --- |
| 5 | example 1 | 0.53 | 4.6.10$^7$ | 133 |
| 6 | example 2 | 0.4 | 3.5.10$^7$ | 133 |
| 7 | example 3 | 0.67 | 5.8.10$^7$ | 132 |
| 8 | example 4 | 0.67 | 5.8.10$^7$ | 131 |

EXAMPLES 9 and 10

These examples are related to the polymerization of ethylene using the catalysts described in examples 1 and 2. The polymerization conditions are as follows: Zr=2 μmol; monomer partial pressure=10 bars (solvent=hexane), methylaluminoxane is used in a ratio Al/Zr of 15000:1, polymerization temperature =70° C., duration=1h. The activity of the catalyst is expressed in g of polymer/mol Zr*hour. The molecular weight distribution (Mw/Mn) is determined by gel permeation chromatography measured at 135° C. using a trichlorobenzene solution with 0.5 g/l of a polymer concentration and a polystyrene gel column, e.g. Waters Styragel HMW 6E available from Waters Co. Ltd. As a measuring device, GPC-150C manufactured by Waters Co Ltd is used for instance.

The results of these tests are given in Table 2 hereunder.

TABLE 2

| Example | Catalyst | Activity | Zr ashes | Mw | Mn | Mw/Mn |
| --- | --- | --- | --- | --- | --- | --- |
| 9 | example 1 | 12.2 * 10$^7$ | 0.75 | 54000 | 12000 | 4.6 (broad) |
| 10 | example 2 | 3 * 10$^7$ | 3 | 271000 | 35000 | 7.8 (bimodal) |

What is claimed is:
1. Metallocenes of formula

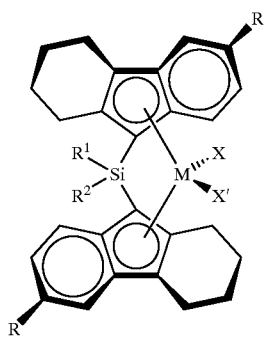

wherein R is chosen from alkyl having from 1 to 3 carbon atoms, M is zirconium, X and X' are chlorine atoms and R$^1$ and R$^2$ are alkyl radicals containing 1 to 3 carbon atoms.

* * * * *